(12) United States Patent
Lee et al.

(10) Patent No.: US 11,752,393 B2
(45) Date of Patent: Sep. 12, 2023

(54) BALANCE TRAINING METHOD USING WEARABLE DEVICE AND THE WEARABLE DEVICE

(71) Applicant: Samsung Electronics Co., Ltd., Suwon-si (KR)

(72) Inventors: Jusuk Lee, Suwon-si (KR); Youn Baek Lee, Yongin-si (KR); Bokman Lim, Hwaseong-si (KR); Seungyong Hyung, Yongin-si (KR); Kyung-Rock Kim, Seoul (KR); Keehong Seo, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 647 days.

(21) Appl. No.: 16/817,090

(22) Filed: Mar. 12, 2020

(65) Prior Publication Data
US 2021/0121741 A1   Apr. 29, 2021

(30) Foreign Application Priority Data

Oct. 28, 2019   (KR) .......................... 10-2019-0134686

(51) Int. Cl.
| | |
|---|---|
| A61B 5/11 | (2006.01) |
| A61B 5/00 | (2006.01) |
| A63B 26/00 | (2006.01) |
| A61H 1/02 | (2006.01) |
| A63B 24/00 | (2006.01) |

(52) U.S. Cl.
CPC ............ *A63B 26/003* (2013.01); *A61B 5/112* (2013.01); *A61B 5/1117* (2013.01); *A61B 5/7275* (2013.01); *A61H 1/0244* (2013.01); *A63B 24/0087* (2013.01); *A63B 2220/54* (2013.01);

(Continued)

(58) Field of Classification Search
None
See application file for complete search history.

(56) References Cited

U.S. PATENT DOCUMENTS

| | | | | |
|---|---|---|---|---|
| 4,934,694 A | * | 6/1990 | McIntosh ............. | A63B 21/154 |
| | | | | 73/379.06 |
| 9,314,393 B2 | * | 4/2016 | Kim .................... | A61N 1/36031 |

(Continued)

FOREIGN PATENT DOCUMENTS

| | | | |
|---|---|---|---|
| JP | 2006-061460 A | | 3/2006 |
| KR | 10-2011-0107420 A | | 10/2011 |

(Continued)

OTHER PUBLICATIONS

Gerards et al., "Perturbation-based balance training for falls reduction among older adults: Current evidence and implications for clinical practice", Geriatrics Gerontology International, vol. 17, pp. 2294-2303 (2017).

(Continued)

*Primary Examiner* — Nyca T Nguyen
(74) *Attorney, Agent, or Firm* — HARNESS, DICKEY & PIERCE, P.L.C.

(57) ABSTRACT

A balance training method using a wearable device, and the wearable device are disclosed. The balance training method using the wearable device configured to provide a walking assist function includes executing a balance training mode of the wearable device and supplying an irregular pattern torque to an actuator of the wearable device at a time point or in a time period in the balance training mode.

19 Claims, 10 Drawing Sheets

(52) U.S. Cl.
CPC ... *A63B 2220/803* (2013.01); *A63B 2220/836* (2013.01)

(56) References Cited

U.S. PATENT DOCUMENTS

| | | | |
|---|---|---|---|
| 2012/0310122 A1* | 12/2012 | Endo | A61H 3/00 601/35 |
| 2015/0209212 A1 | 7/2015 | Duguid | |
| 2015/0272809 A1* | 10/2015 | Accoto | A61H 1/0237 623/31 |
| 2015/0321342 A1* | 11/2015 | Smith | B25J 9/0006 74/490.03 |
| 2016/0113831 A1* | 4/2016 | Hollander | A61H 3/00 623/32 |
| 2017/0312579 A1* | 11/2017 | Nakashima | A63B 21/00181 |
| 2018/0104075 A1* | 4/2018 | Mooney | A61H 1/024 |
| 2018/0147108 A1* | 5/2018 | Lee | A61H 1/0244 |
| 2020/0214925 A1* | 7/2020 | Lim | A61H 1/024 |
| 2021/0121729 A1* | 4/2021 | Kim | A63B 21/0059 |
| 2021/0128972 A1* | 5/2021 | Lee | A63B 21/00181 |

FOREIGN PATENT DOCUMENTS

| | | |
|---|---|---|
| KR | 10-2017-0019175 A | 2/2017 |
| WO | WO-2016/077442 A1 | 5/2016 |

OTHER PUBLICATIONS

Extended European Search Report dated Feb. 22, 2021, for corresponding EP Application No. 20192598.9.

* cited by examiner

BALANCE TRAINING METHOD USING WEARABLE DEVICE AND THE WEARABLE DEVICE

CROSS-REFERENCE TO RELATED APPLICATION

This application claims under 35 U.S.C. § 119 to Korean Patent Application No. 10-2019-0134686 filed on Oct. 28, 2019, in the Korean Intellectual Property Office, the entire contents of which are incorporated herein by reference in their entirety.

BACKGROUND

1. Field

At least one example embodiment relates to a balance training method using a wearable device.

2. Description of the Related Art

A person may instinctively perform anticipatory and compensatory postural adjustment based on a mutual balance between sensory information and an exercise. However, a sensory capacity and an exercise capacity of a person may gradually deteriorate with age. Thus, an elderly person may experience more difficulty in walking and have a higher risk of tripping or falling while he/she is walking. There are various preventive methods for falls, for example, doing a physical exercise to improve muscular strength and flexibility of the body, changing an environment by brightening more lights and installing an anti-slip pad, and using an assistance device such as a cane and low-heeled shoes. Alternatively, there are other methods that train a person to be strong enough to resist an external force. For example, a medical staff may push a target person from the side by applying a force directly to the person with hands while the person is walking, or shake a platform while the person is walking on the platform, or may separately control a speed of a left-sided running belt and a speed of a right-sided running belt of a treadmill to train a person.

SUMMARY

At least one example embodiment relates to a balance training method using a wearable device.

In some example embodiments, the balance training method includes generating, during a balance training mode of the wearable device, an irregular torque pattern; supplying the irregular torque pattern to an actuator of the wearable device; and outputting, via the actuator, a torque based on the irregular torque pattern.

In some example embodiments, the balance training method includes generating, a walking assistance torque pattern associated with providing a walking assist function to a user wearing the wearable device during a first time period, wherein the irregular torque pattern is a pattern to which a perturbation is applied in a second time period, wherein the perturbation is not applied to walking assistance torque pattern supplied to the actuator in the first time period.

In some example embodiments, the generating includes generating the irregular torque pattern by applying the perturbation to the walking assistance torque pattern such that, during the second time period, the torque output by the actuator includes a sudden change in force.

In some example embodiments, the generating includes generating the walking assistance torque pattern based on a gait cycle of the user wearing the wearable device; determining the perturbation; and applying the perturbation to the walking assistance torque pattern.

In some example embodiments, the determining the perturbation includes determining a strength change and an offset change of the perturbation based on an elapsed time, and wherein the generating of the irregular torque pattern includes generating the irregular torque pattern by applying, to the walking assistance torque pattern, the strength change and the offset change of the perturbation.

In some example embodiments, the balance training method includes detecting a reaction of a user wearing the wearable device to the irregular torque pattern being supplied to the actuator; and adjusting the irregular torque pattern based on the reaction of the user.

In some example embodiments, the adjusting includes adjusting at least one of a frequency rate, a strength, or a pattern of a perturbation associated with to the irregular torque pattern.

In some example embodiments, the detecting includes determining a recovery index indicating a degree of recovery from the irregular torque pattern based on sensing information measured by the wearable device, wherein the adjusting adjusts the perturbation associated with the irregular torque pattern, when the recovery index satisfies a set requirement.

In some example embodiments, the detecting includes determining a potential fall index indicating a probability of the user falling based on sensing information measured by the wearable device, wherein the adjusting adjusts a torque to be supplied to the actuator based on a safety torque pattern corresponding to a safety mode of the wearable device, when the potential fall index satisfies a set requirement.

In some example embodiments, the detecting includes determining a potential fall index indicating a probability of the user falling based on sensing information measured by the wearable device, wherein the adjusting includes blocking a torque from being supplied to the actuator, when the potential fall index satisfies a set requirement.

In some example embodiments, the supplying includes determining a time point at which a perturbation is to be applied to the irregular torque pattern; generating the irregular torque pattern by applying the perturbation to a walking assistance torque pattern at the time point; and supplying the irregular torque pattern to the actuator.

In some example embodiments, the determining of the time point includes determining, to be the time point, a time point at which a step count of a user wearing the wearable device reaches a set step count.

In some example embodiments, the determining of the time point includes detecting whether a user wearing the wearable device recovers from the irregular torque pattern and reaches a steady state based on sensing information measured by the wearable device; and determining, to be the time point, a time point in a time period in which the user wearing the wearable device reaches the steady state.

In some example embodiments, the determining of the time point includes determining the time point at which the perturbation is to be applied based on an operation signal received from a remote operation device configured to communicate with the wearable device.

Some example embodiments relate to a non-transitory computer-readable medium comprising computer readable instructions to cause a computer to perform the balance training method.

Some example embodiments relate to a wearable device configured to provide a walking assist function.

In some example embodiments, the wearable device includes a sensor configured to measure a movement of a user wearing the wearable device; a controller configured to execute a balance training mode of the wearable device by generating an irregular torque pattern; and an actuator configured to output a torque based on the irregular torque pattern.

In some example embodiments, the controller is configured to generate, a walking assistance torque pattern associated with providing the walking assist function to the user during a first time period; generate the irregular torque pattern by applying a perturbation to the walking assistance torque pattern in a second time period; and supply the irregular torque pattern to the actuator such that, during the second time period, the irregular torque output by the actuator includes a sudden change in force.

In some example embodiments, the controller is configured to detect a reaction of the user wearing the wearable device to the irregular torque pattern being supplied to the actuator based on sensing information measured by the sensor; and adjust the irregular torque pattern based on the reaction of the user.

In some example embodiments, the controller is configured to determine a time point at which a perturbation is to be applied to the irregular torque pattern; generate the irregular torque pattern by applying the perturbation to a walking assistance torque at the time point; and supply the irregular torque pattern to the actuator.

In some example embodiments, the controller is configured to determine, to be the time point, a time point at which a step count of the user wearing the wearable device reaches a set step count or a time point at which the user wearing the wearable device recovers from the irregular torque pattern and reaches a steady state.

In some example embodiments, the wearable device includes a communicator configured to communicate with a remote operation device, wherein the controller is configured to determine the time point at which the perturbation is to be applied based on an operation signal received from the remote operation device.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
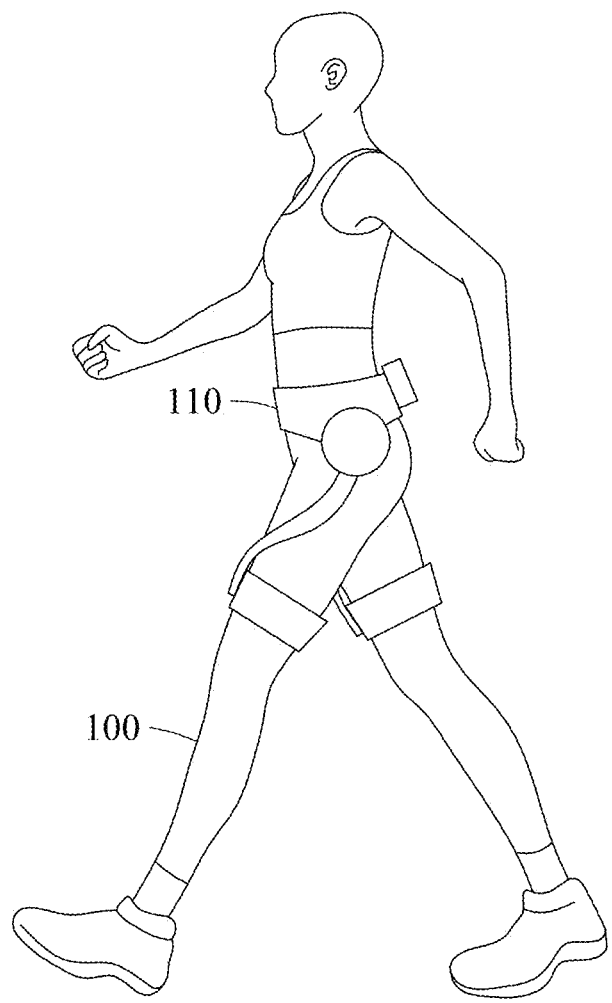
FIG. 1 is a diagram illustrating an example of a wearable device worn on a user according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

Hereinafter, examples will be described in detail with reference to the accompanying drawings, and like reference numerals in the drawings refer to like elements throughout.

FIG. 1 is a diagram illustrating an example of a wearable device worn on a user according to at least one example embodiment.

Referring to FIG. 1, a wearable device 110 is configured to perform a function of assisting a user 100 wearing the wearable device 110 in walking more readily. The wearable device 110 may also be referred to as a walking assist device or a gait assist device. When the wearable device 110 is provided to perform such walking assist function, the wearable device 110 may assist or support an entire leg of the user 100 or a portion of the leg to help the user 100 walk more readily. For example, when a person including, for example, an elderly person, wears the wearable device 110, the wearable device 110 may help the person walk for a longer period of time to enhance an ability to walk or improve an abnormal gait of the person. In addition, the wearable device 110 may provide a force needed for the person to walk, enabling the person to walk independently.

The wearable device 110 may be provided in a wearable exoskeleton type as illustrated in FIG. 1, and configured to assist or support a muscular strength of the user 100 when the user 100 walks and thus to improve a walking movement or a gait of the user 100 or enable the user 100 to walk normally. For example, the wearable device 110 is provided in a hip type that is worn on a hip joint or a thigh as illustrated in FIG. 1. However, a type of the wearable device 110 is not limited to the illustrated example, and other types may also be applicable to the wearable device 110. For example, the wearable device 110 may be provided in a type that assists or supports an entire leg including a hip, a knee, and an ankle, or in a type that assists or supports a portion of the leg, for example, an ankle or a knee.

According to an example, the wearable device 110 may also perform an exercise function by providing a resistance force to the user 100. The resistance force acts as a force that hinders the user 100 in moving to help increase a muscular strength of the user 100. For example, the wearable device 110 may generate a resistance torque to provide resistance to the user 100 while the user 100 is walking, and apply the resistance force to a movement of the user 100 based on the generated resistance torque.

The wearable device 110 may also be used to provide balance training to the user 100. The wearable device 110 may perform a balance training mode, and provide the user 100 with a training function in the balance training mode to train the user 100 to inhibit (or, alternatively, prevent) the user 100 from falling. For example, the wearable device 110 may perform perturbation-based balance training (PBT) by applying an irregular pattern force, for example, an assistance force or a resistance force, to the user 100 when the user 100 performs an action, for example, walks or does an exercise, while wearing the wearable device 110. In this example, the wearable device 110 may generate a perturbation to simulate a situation where a fall occurs. The wearable device 110 may simulate a similar situation to a situation where an actual fall occurs by applying, to the user 100, an irregular pattern force, for example, a force that is not expected or perceived in advance by the user 100.

According to an example embodiment, there is provided a method of performing the fall prevention training using the wearable device 110. When the user 100 moves while wearing the wearable device 110, the wearable device 110 may apply an irregular assistance force and/or an irregular resistance force to the movement of the user 100 in order to simulate an actual situation in which a fall occurs. In the simulated situation, the user 100 may be trained to react to such a situation repeatedly, and thus may grow strong against an unexpected external force and improve an ability to react to an actual falling situation more rapidly and safely.

The user 100 may develop an ability to react to or control the irregular pattern force transferred from the wearable device 110 in the balance training mode, and thus may enhance an ability to avoid a potential risk of falling that may occur in daily life. For example, an elderly person may fall while moving due to a difference between will and action, and the wearable device 110 may generate such a difference artificially and enable the user 100 to overcome a fall that may otherwise occur due to the difference. The wearable device 110 may enhance user's 100 a sense of balance and an ability to react by the user responding to potential falls that are simulated and provided by the wearable device 110.

Such a balance training function of the wearable device 110 may be effectively performed for a general person and an athlete in addition to an elderly person and a patient. In addition, unlike a treadmill, the wearable device 110 may provide the balance training function in various environments or locations, without a restriction on environment or location. Further, the wearable device 110 may provide the balance training function for various actions, for example, sitting, standing, jumping, and squatting, in addition to walking.

Figure 2:
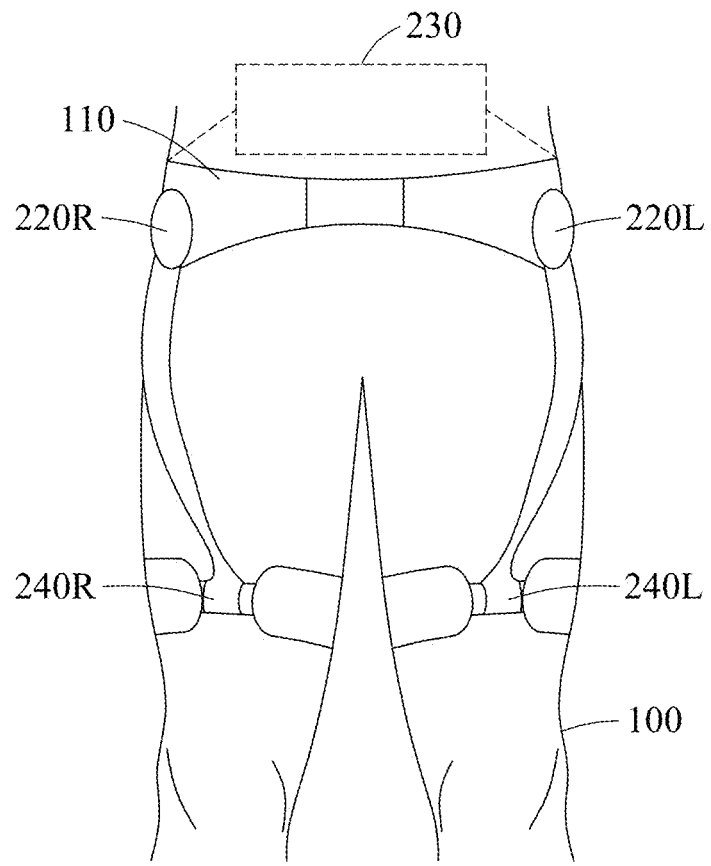
FIG. 2 is a diagram illustrating an example of a structure of a wearable device according to at least one example embodiment.

FIG. 2 is a diagram illustrating an example of a structure of a wearable device according to at least one example embodiment.

Referring to FIG. 2, a wearable device 110 generates a walking assistance torque at left and right hip joint portions 220L and 220R under the control of a controller 230, and the generated walking assistance torque provides legs of a user 100 with power for flexion and extension through transferrers 240L and 240R disposed above knees of the user 100. The controller 230 measures movement information of the user 100 through a sensor, and estimates a gait phase or a gait state in a gait cycle of the user 100 based on the measured movement information. The controller 230 determines a direction in which power is to be provided to each of the legs and an amount of the power to be provided at a current time point, based on the estimated gait phase.

According to an example embodiment, when a balance training function is performed while the user 100 is walking, the wearable device 110 may generate an irregular pattern torque by adding a perturbation to a walking assistance torque to be applied to the user 100. The irregular pattern torque may act as an assistance force and/or a resistance force that is not expected by the user 100 while the user 100 is moving. The user 100 may react to the unexpected assistance force or resistance force, and thus enhance an ability to be prepared for a situation in which a fall occurs due to a sudden change in force.

Figure 3:
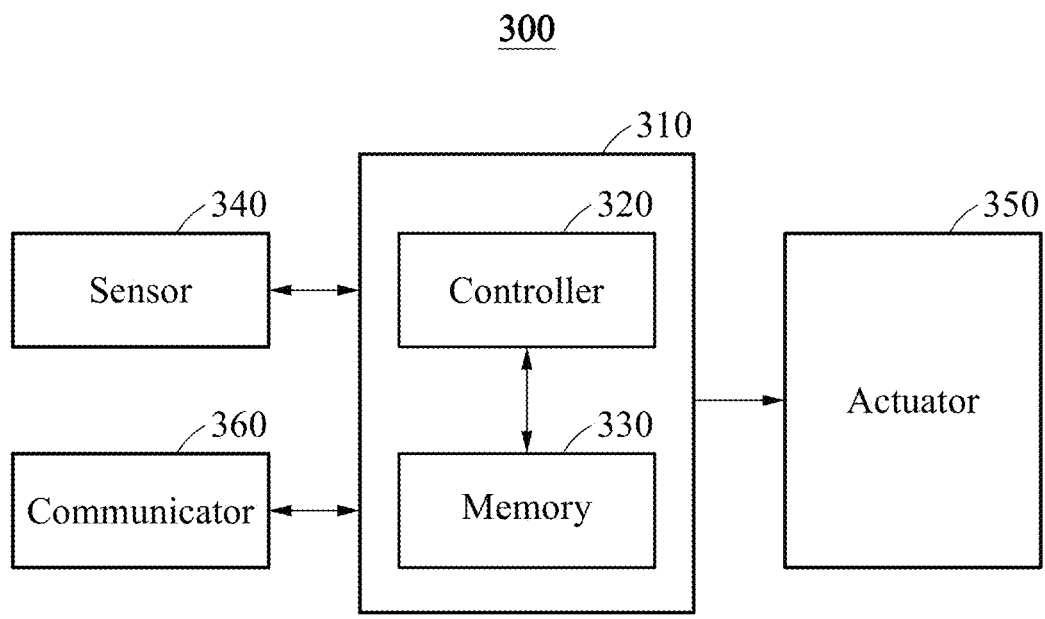
FIG. 3 is a diagram illustrating an example of a configuration of a wearable device according to at least one example embodiment.

FIG. 3 is a diagram illustrating an example of a configuration of a wearable device according to at least one example embodiment.

Referring to FIG. 3, a wearable device 300 includes at least one sensor 340, a control device 310, and an actuator 350. According to an example, the wearable device 300 may further include a communicator 360 configured to communicate with an external device, for example, a remote operation device.

The sensor 340 may include various sensors. For example, the sensor 340 may include a sensor configured to measure a gait or a movement of a user wearing the wearable device 300, and a sensor configured to measure information needed to control an operation of the wearable device 300. The sensor 340 may include, for example, an acceleration sensor, an inertial sensor, and/or a gyro sensor to measure a movement of the user. The sensor 340 may also include, for example, a torque sensor and/or a current/voltage sensor to measure a torque transferred through the actuator 350.

The control device 310 configured to control an operation and a function of the wearable device 300 includes a controller 320 and a memory 330. The memory 330 is connected to the controller 320, and configured to store instructions to be executed by the controller 320, and data to be processed by the controller 320 and/or data having been processed by the controller 320. For example, the memory 330 stores parameters corresponding to a control signal output by the controller 320. The memory 330 may include a non-transitory computer-readable storage medium, for example, a high-speed random-access memory (RAM) and/or a nonvolatile computer-readable storage medium (e.g., at least one disk storage device, flash memory device, or other nonvolatile solid-state memory devices).

The controller 320 generates a control signal to control the wearable device 300. For example, the controller 320 generates a torque control signal to control a torque to be provided by the wearable device 300 based on a movement of the user measured by the sensor 340. The controller 320 performs one or more, or all, of operations and functions of a wearable device described herein.

The controller 320 may be implemented using processing circuitry such as hardware including logic circuits, a hardware/software combination such as a processor executing software; or a combination thereof. For example, the processing circuitry may include, but is not limited to, a central processing unit (CPU), an arithmetic logic unit (ALU), a digital signal processor, a microcomputer, a field programmable gate array (FPGA), a system-on-chip (SoC), a programmable logic unit, a microprocessor, or an application-specific integrated circuit (ASIC), etc.

The actuator 350 outputs a torque based on the torque control signal generated by the controller 320. The actuator 350 provides a specific force, for example, an assistance force and/or a resistance force, to a movement of both hip joints of the user. The actuator 350 converts electrical energy to kinetic energy, and applies the kinetic energy to a body of the user to provide the user with a force needed for the user to move or provide the user with a force hindering the user from moving. The actuator 350 may be disposed on a portion corresponding to positions of the hip joints of the user, for example, the one or more of the hip joint portions 220R, 220L, and generate a torque for flexion and extension of legs of the user.

When the wearable device 300 operates in a walking assist mode in which a walking assist function is performed, the controller 320 controls the actuator 350 configured to generate a walking assistance torque through the control signal. The controller 320 determines a state variable indicating a gait phase or a gait state of the user based on a walking movement of the user and controls the actuator 350 based on the determined state variable. The controller 320 sets a parameter to control the walking assistance torque based on the state variable and outputs the torque control signal to assist the user in walking based on the set parameter.

According to an example embodiment, the controller 320 controls a walking assistance torque to be provided by the wearable device 300 based on a state variable, and determines a control signal to control the walking assistance torque based on the state variable. The controller 320 sets a gain to adjust a strength of the walking assistance torque and sets a time delay to adjust an output time of the walking assistance torque. The controller 320 then defines the state variable based on the set gain and the set time delay.

According to an example, there may be a remote operation device (not shown) configured to remotely control the wearable device 300. The remote operation device may control an overall operation of the wearable device 300 in response to a user input. For example, the remote operation device may start or end, or resume or suspend, a certain function or operation of the wearable device 300. The remote operation device may provide a user interface (UI) that enables an operation or manipulation of the wearable device 300, and control a function and operation of the wearable device 300 through the UI.

According to an example embodiment, the wearable device 300 operates in a balance training mode to perform a balance training function. The balance training mode may be triggered by an input from the user wearing the wearable device 300 or from another person, for example, a medical staff or a rehabilitation therapist. The input may indicate an execution of the balance training mode. The input may be made by a manipulation through an operation interface of the wearable device 300 or the UI of the remote operation device, for example.

In response to the input being received, the controller 320 executes the balance training mode of the wearable device 300 and generates an irregular pattern torque at one time point or in one time period in the balance training mode. For example, the controller 320 may generate a torque with an irregular pattern at one certain time point or in one time period while generating a normal walking assistance torque with a regular pattern. The irregular pattern torque may indicate a torque to which a perturbation is applied. The perturbation may be one that is not applied to a pattern of a torque supplied to the actuator 350 in a previous time period. The controller 320 generates the irregular pattern torque to which the perturbation is applied and supplies the generated irregular pattern torque to the actuator 350. The actuator 350 outputs the irregular pattern torque generated by the controller 320, thereby applying an irregular pattern force to the user wearing the wearable device 300.

According to an example embodiment, the controller 320 generates the irregular pattern torque by determining a time point at which the perturbation is to be applied to the irregular pattern torque and applying the perturbation to a walking assistance torque at the determined time point. For example, the controller 320 applies the perturbation to the walking assistance torque at a time point at which a step count of the user wearing the wearable device 300 reaches a set step count. For another example, the controller 320 determines whether the user wearing the wearable device 300 walks in a steady state based on sensing information, for example, movement information, that is measured through the sensor 340 of the wearable device 300, and determines, to be the time point at which the perturbation is to be applied, a time point in a time period in which the walking of the user is determined to be in the steady state. For another example, the controller 320 may randomly determine the time point at which the perturbation is to be applied. To randomly determine the time point at which the perturbation is to be applied or a strength of the perturbation, a random function, for example, a rand function, may be used. For still another example, the controller 320 determines the time point at which the perturbation is to be applied based on an operation signal received from the remote operation device. When receiving the operation signal indicating an instruction to generate the perturbation from the remote operation device through the communicator 360, the controller 320 generates the irregular pattern torque to which the perturbation is applied at a time point at which the operation signal is received.

The strength of the perturbation may be determined randomly within a set range, for example. Alternatively, the perturbation may have a desired (or, alternatively, a preset) strength. Further, whether the strength starts at a random or desired level, the strength of the perturbation may vary over time.

According to another example embodiment, the controller 320 detects a reaction of the user wearing the wearable device 300 to the irregular pattern torque being supplied to the actuator 350 based on sensing information measured by the sensor 340. The irregular pattern torque may also be referred to as a balance training torque. The controller 320 then adjusts a torque to be supplied to the actuator 350 based on the detected reaction of the user. For example, the controller 320 determines whether the user keeps his/her balance or recovers to be in a normal posture in response to the irregular pattern torque, based on movement information of the user. Based on the reaction of the user to the irregular pattern torque, the controller 320 adjusts a frequency rate, a strength, and/or a pattern of a perturbation to be applied to a torque to be supplied to the actuator 350 in the future. In this example, when the controller 320 determines that the user does not readily keep his/her balance or recover to be in the normal posture in response to an irregular pattern torque previously supplied, the controller 320 decreases, as part of the adjustment, the strength or the frequency rate of the perturbation than before. In contrast, when the controller 320 determines that the user keeps readily his/her balance or recovers to be in the normal posture in response to the irregular pattern torque, the controller 320 increases, as part of the adjustment, the strength or the frequency rate of the perturbation than before. As described above, the controller 320 may generate a balance training torque adaptive to a movement of a user wearing the wearable device 300, and thus provide various forms of balance training torques that are customized for the user.

Figure 4:
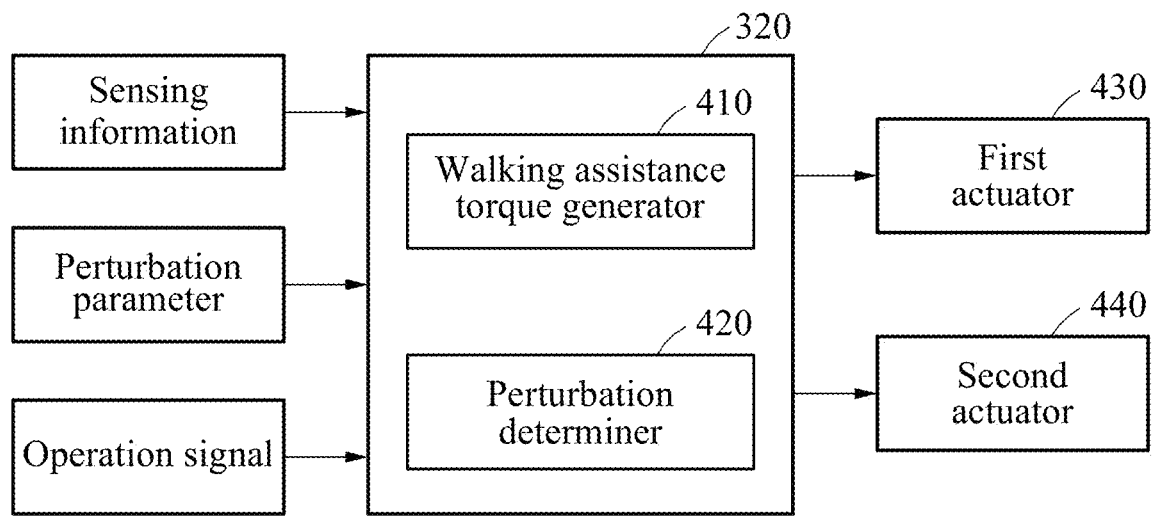
FIG. 4 is a diagram illustrating an example of an operation of a controller of a wearable device according to at least one example embodiment.

FIG. 4 is a diagram illustrating an example of an operation of a controller of a wearable device according to at least one example embodiment.

Referring to FIG. 4, the controller 320 of the wearable device includes a walking assistance torque generator 410 and a perturbation determiner 420. The walking assistance torque generator 410 generates a walking assistance torque based on sensing information measured by a sensor. The walking assistance torque generator 410 estimates a gait cycle of a user wearing the wearable device based on the sensing information, and determines the walking assistance torque based on a gait phase of the user based on the estimated gait cycle. For example, the walking assistance torque generator 410 determines the walking assistance torque to be supplied to a first actuator 430 and the walking assistance torque to be applied to a second actuator 440. For example, the first actuator 430 and the second actuator 440 may be included in the actuator 350 illustrated in FIG. 3. The first actuator 430 may provide a force to a right leg of the user, and the second actuator 440 may provide a force to a left leg of the user. The first actuator 430 and the second actuator 440 may be located at respective ones of the hip joint portions 220R, 220L.

The perturbation determiner 420 determines a perturbation to be applied to an irregular pattern torque based on a perturbation parameter or an operation signal received from, for example, the wearable device or the remote operation device. The perturbation parameter may include setting values, for example, a time point at which the perturbation is to be applied, a frequency rate indicating how frequently the perturbation is to be applied, a variation indicating how many various patterns of the perturbation are to be applied, and a strength indicating how strongly the perturbation is to be applied. For the time point at which the perturbation is to be applied, the perturbation may be set to be applied to a certain gait phase in the gait cycle of the user. The perturbation parameter may be determined randomly depending on a situation or set in advance. The operation signal may include information that controls the perturbation to be applied to at least one of the first actuator 430 and the second actuator 440 at a time point triggered by a manual operation, for example, an operation or manipulation on a button or an interface of the wearable device or the remote operation device.

According to an example embodiment, the perturbation determined by the perturbation determiner 420 is applied to the walking assistance torque, thereby the irregular pattern torque is generated. The walking assistance torque may exhibit a regular pattern based on a repeating gait cycle of the user. Thus, when the perturbation is applied to the walking assistance torque, the walking assistance torque with the regular pattern may be transformed into the irregular pattern torque with an irregular pattern. According to another example embodiment, the perturbation determined by the perturbation determiner 420 is applied to an exercise performance torque, thereby the irregular pattern torque is generated. The exercise performance torque may also exhibit a regular pattern based on a repeating exercise movement performed by the user. Thus, when the perturbation is applied to the exercise performance torque, the exercise performance torque with the regular pattern may be transformed into the irregular pattern torque with an irregular pattern.

The controller 320 may implement a simulated or similar situation where a fall occurs by rapidly changing a torque value of an actuator or a motor corresponding to each joint of the user through such a perturbation. Such a rapid change of the torque value may be triggered by a manual operation of, for example, the remote operation device. In addition, a time point at which the rapid change of the torque value by the perturbation occurs and a strength of the torque value may be automatically set through a random function or automatically determined based on a gait phase of the user based on sensing information including, for example, joint angle information and movement information of the user.

In addition, a strength of the perturbation may be adjusted based on a condition of the user or a balance training step, and a range of the strength may be restricted such that the perturbation is applied at a relatively low strength not to cause an actual fall during balance training.

Figure 5:
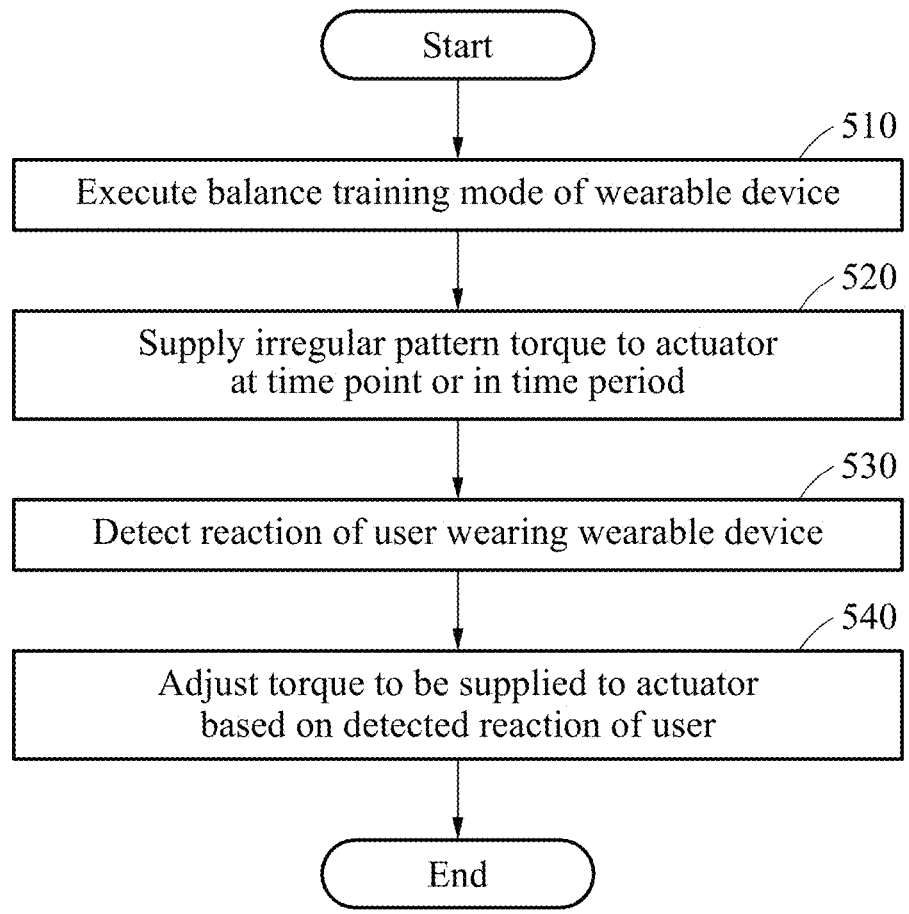
FIG. 5 is a flowchart illustrating an example of a balance training method using a wearable device according to at least one example embodiment.

FIG. 5 is a flowchart illustrating an example of a balance training method using a wearable device according to at least one example embodiment. The balance training method may be performed by a controller of the wearable device.

Referring to FIG. 5, in operation 510, the controller 320 executes a balance training mode of the wearable device. The balance training mode may be triggered by an input from a user wearing the wearable device or by an input from another person. Alternatively, the balance training model may be triggered by an operation signal received from the remote operation device that communicates with the wearable device.

In operation 520, the controller 320 supplies an irregular pattern torque to an actuator of the wearable device at one time point or in one time period in the balance training mode. The controller 320 generates the irregular pattern torque by determining a perturbation that is not applied to a pattern of a torque previously supplied to the actuator in a previous time period and applying the determined perturbation to a torque to be supplied to the actuator.

According to an example embodiment, the controller 320 generates a walking assistance torque based on a gait cycle of the user and determines the perturbation, and then generates the irregular pattern torque by applying the determined perturbation to the generated walking assistance torque. Here, to determine the perturbation, the controller 320 may randomly determine a characteristic of the perturbation using a random function or determine the perturbation using a set perturbation parameter (e.g., a strength of the perturbation and a time point at which the perturbation is to be applied). When using the random function, there may be a restriction associated with a frequency rate or a strength of the perturbation. Alternatively, the controller 320 may determine the perturbation based on movement information of the user or an operation signal received from the remote operation device.

Here, various methods may be used to determine a time point at which the perturbation is to be applied or supplied to the actuator, that is a time point at which a variation or a change of a torque value that is not expected by the user is to be applied to the actuator. For example, the controller 320 may determine the time point to be a time point at which a step count of the user wearing the wearable device reaches a set step count. The set step count may be the number of walking steps of the user that is set in advance or determined randomly. For another example, the controller 320 may determine the time point at which the perturbation is to be applied based on the operation signal received from, for example, the remote operation device. In this example, the controller 320 may determine the time point to be a time point triggered by a button of the remote operation device being pressed. For still another example, the controller 320 may determine the time point to be a time point at which the user wearing the wearable device is determined to walk in a steady state based on sensing information. The controller 320 may then generate the irregular pattern torque by applying the perturbation to the walking assistance torque at the time point determined as described in the foregoing.

According to another example embodiment, the controller 320 determines a strength change and an offset change of the perturbation based on an elapsed time. The strength change and the offset change of the perturbation may be determined by a random function, for example. The controller 320 generates the irregular pattern torque by applying the determined strength change and offset change of the perturbation to the walking assistance torque. For example, the controller 320 may generate the irregular pattern torque by multiplying a strength of the walking assistance torque by a strength of the perturbation and by adding an offset to a resultant value of the multiplying.

The controller 320 may supply the irregular pattern torque generated as described in the foregoing to at least one of actuators included in the wearable device.

According to some example embodiments, the controller 320 may further perform detection of an abort signal while supplying an irregular torque pattern to the actuator, and, in response to the abort signal, may either stop providing torque to the user or may switch from providing the irregular torque pattern to outputting a recovery assistance torque pattern to the user to assist the user in recovering from a potential fall.

For example the controller 320 may evaluate gait data such as a gait symmetry, a stride length of the user, a stride width, a foot clearance, a landing speed, and a walk ratio of the user, and generate evaluation values of the same.

The controller 320 may generate the recovery assistance torque pattern such that the recovery assistance torque pattern effectively recovers the user's gait back to a stable gait based on the evaluation values of the gait data.

According to some example embodiment, the controller 320 may further perform subsequent operations 530 and 540. In operation 530, the controller 320 detects a reaction of the user wearing the wearable device to the irregular pattern torque being supplied to the actuator. In operation 540, the controller 320 adjusts a torque to be supplied to the actuator based on the reaction of the user detected in operation 530. For example, the controller 320 may adjust at least one of a frequency rate, a strength, or a pattern of the perturbation to be applied to the irregular pattern torque.

According to an example embodiment, in operation 530, the controller 320 determines a recovery index indicating a degree of how much the user recovers from the irregular pattern torque being applied based on sensing information measured by the wearable device. In operation 540, when the recovery index satisfies a set requirement, the controller 320 adjusts the perturbation to be applied to the irregular pattern torque. For example, the controller 320 may measure the recovery index based on a similarity between a walking movement of the user after the perturbation is applied and a walking movement of the user when there is no perturbation, based on the sensing information. The controller 320 may determine a degree of how much the user recovers from the perturbation by determining whether the user follows an anticipated walking movement after the perturbation is applied, based on the sensing information. For example, when the recovery index of the user is less than a desired (or, alternatively, a preset) first reference value, the controller 320 may decrease a strength of a perturbation to be applied next. When the recovery index of the user is greater than a preset second reference value, the controller 320 may increase the strength of the perturbation to be applied next.

According to another example embodiment, in operation 530, the controller 320 determines a potential fall index indicating a probability of the user falling based on sensing information measured by the wearable device. In operation 540, when the potential fall index satisfies a set requirement, the controller 320 adjusts the torque to be applied to the actuator based on a torque profile corresponding to a safety mode of the wearable device. For example, the controller 320 may estimate a posture and a leg movement of the user based on movement information of the user after the perturbation is applied, and determine the potential fall index based on the estimated posture and leg movement. When the potential fall index is greater than a reference value, the controller 320 may block the torque from being supplied to the actuator, or supply, to the actuator, a torque that enables the user to assume a stable posture again. Alternatively, the controller 320 may adjust a strength of a perturbation to be applied next or a time point at which a perturbation is to be applied next. As described above, when a fall is expected to occur while monitoring a situation in which the balance training method is performed, the controller 320 may block power from being supplied to the actuator, or control the actuator such that the user assumes a stable posture again.

Figure 6:
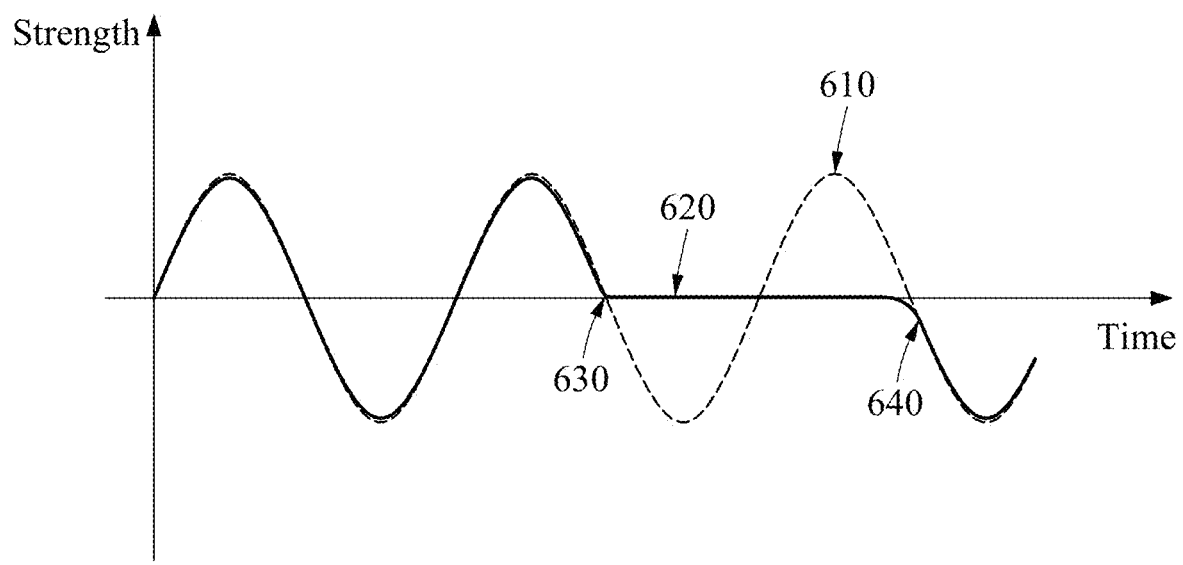
FIG. 6 is a diagram illustrating an example of an irregular pattern torque according to at least one example embodiment.

FIG. 6 is a diagram illustrating an example of an irregular pattern torque according to at least one example embodiment.

Referring to FIG. 6, a walking assistance torque 610 indicates a torque to be output by a controller of a wearable device when it is assumed that a user wearing the wearable device walks according to a regular gait cycle. The walking assistance torque 610 may exhibit a regular pattern based on a regular walking characteristic of the user.

When the wearable device operates in a balance training mode, the controller supplies an irregular pattern torque 620 that is not expected by the user to an actuator of the wearable device at a time point 630 while supplying the walking assistance torque 610 to the actuator. The controller generates the irregular pattern torque 620 by applying a perturbation to the walking assistance torque 610 at the time point 630. The time point 630 at which the perturbation is to be applied may be a time point at which a step count of the user reaches a set step count, a time point at which a triggering signal is received from a remote operation device, or a time point in a time period in which the user walks in a steady state. Alternatively, the time point 630 may be determined randomly. As illustrated, the walking assistance torque 610 with the expected original regular pattern is supplied again from a time point 640 after the irregular pattern torque 620 is supplied. While walking in a steady state, the user may experience a similar situation to an actual situation where a fall occurs in a time period from the time point 630 to the time point 640 in which the irregular pattern torque 620 is supplied to the actuator. Through repeated training on such an experience to react to and recover from a fall, the user may enhance a sense of balance and improve an ability to cope with a fall. For example, as illustrated in FIG. 6, a torque with a strength of 0 may be supplied during a time period after the time point 630 at which the irregular pattern torque 620 is supplied, the user may adapt to a risk of a fall during such time period. After the user adapts to the risk during the time period, a normal assistance torque, for example, the walking assistance torque 610, may be supplied again from the time point 640. Here, the normal assistance torque may be another type of perturbation different from the perturbation to which the user has adapted during the time period, and thus the user may experience the other type of perturbation to enhance further the sense of balance and improve further the ability to cope with a fall.

Figure 7:
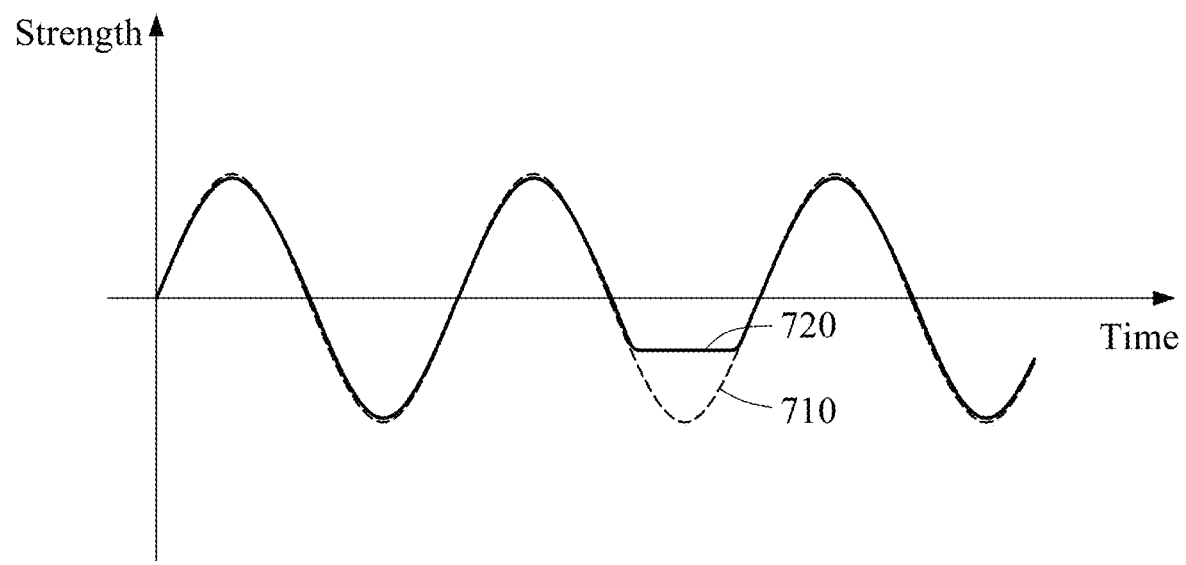
FIGS. 7 through 9 are diagrams illustrating examples of generating an irregular pattern torque according to at least one example embodiment.
Figure 8:
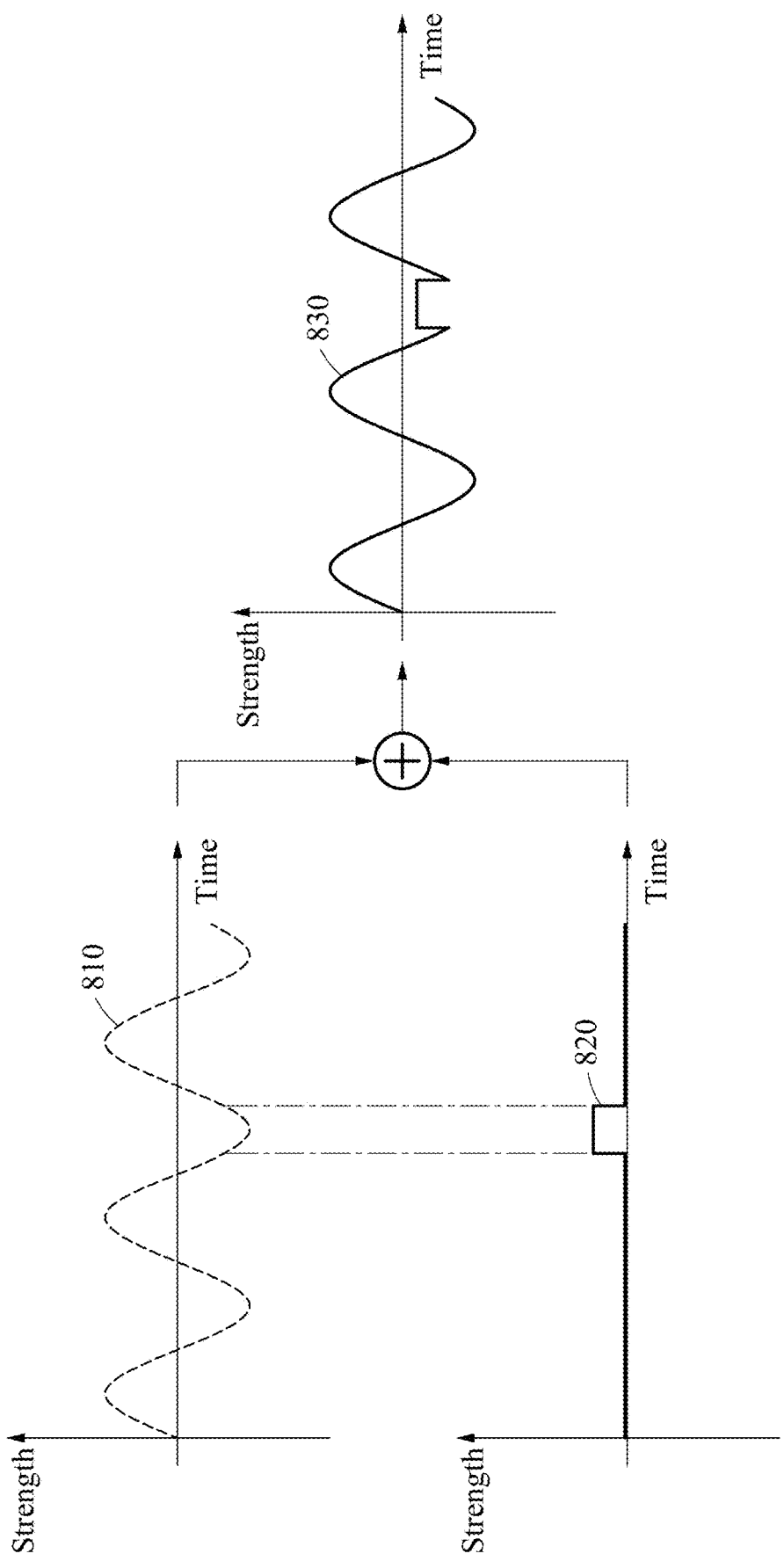
Figure 9:
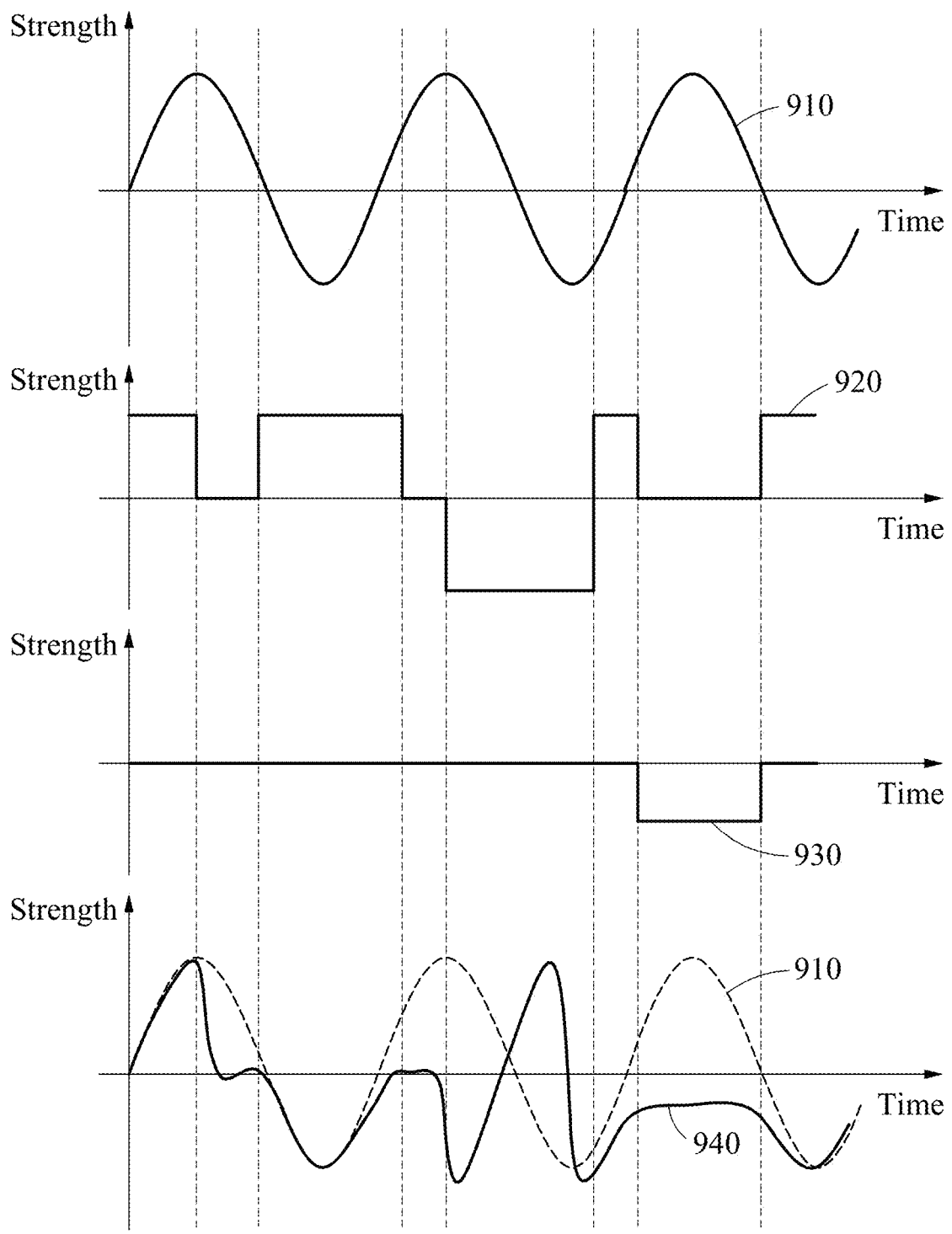

FIGS. 7 through 9 are diagrams illustrating examples of generating an irregular pattern torque according to at least one example embodiment.

Referring to FIG. 7, the controller 320 of a wearable device may generate an irregular pattern torque 720 by changing a variable, for example, a gain or a phase, of an algorithm that generates a walking assistance torque 710 to be applied to an actuator of the wearable device. For example, the controller may generate the irregular pattern torque 720 in a time period by changing a variable used to generate a pattern of the walking assistance torque 710 at a random time point. In this example, a time point at which a perturbation forming an irregular pattern is to be applied may be determined by a random function such as a rand function. As described above, the controller 320 may directly generate an irregular pattern torque to which a perturbation is applied by changing an algorithm used to generate the walking assistance torque 710.

Referring to FIG. 8, the controller 320 may generate an irregular pattern torque 830 by generating a walking assistance torque 810 based on an algorithm used to generate a walking assistance torque, determining a perturbation 820 based on sensing information, and applying the determined perturbation 820 to the generated walking assistance torque 810. For example, the controller 320 may determine a time point at which the perturbation 820 is to be applied through a random function, and a strength of the perturbation 820. The controller 320 may separately generate the walking assistance torque 810 and the perturbation 820, and then generate the irregular pattern torque 830 to be used in a balance training mode by combining or adding the perturbation 820 and the walking assistance torque 810.

Referring to FIG. 9, the controller 320 may generate a walking assistance torque 910 based on an algorithm. The controller may determine a change in a strength 920 (e.g., gain) and a change in an offset 930 of a perturbation based on an elapsed time, using a random function. Examples of the change in the strength 920 and the change in the offset 930 are not limited to a form of square wave as illustrated in FIG. 9, but may have various forms. The controller 320 may generate an irregular pattern torque 940 by multiplying a strength of the walking assistance torque 910 by the strength 920 of the perturbation and adding the offset 930 to a resultant value of the multiplying. For example, the controller 320 may utilize Equation #1 to generate the irregular torque pattern 940 at various times t.

$$\text{Irregular Torque}(t) = (\text{Gain}(t) * \text{Walking Assist Torque}(t)) + \text{Offset}(t) \tag{Eq. \#1}$$

As discussed above, the gain and the offset may be randomly determined, such that the controller 320 may determine the irregular pattern torque 940 based on Equation #2.

$$\text{Irregular Torque}(t) = (\text{Gain}(\text{rand},t) * \text{Walking Assist Torque}(t)) + \text{Offset}(\text{rand},t) \tag{Eq. \#2}$$

In the examples described above with reference to FIGS. 7 through 9, a walking assistance torque may be replaced with an exercise performance torque, and a method of generating an irregular pattern torque may not be limited to the examples described in the foregoing.

Figure 10:
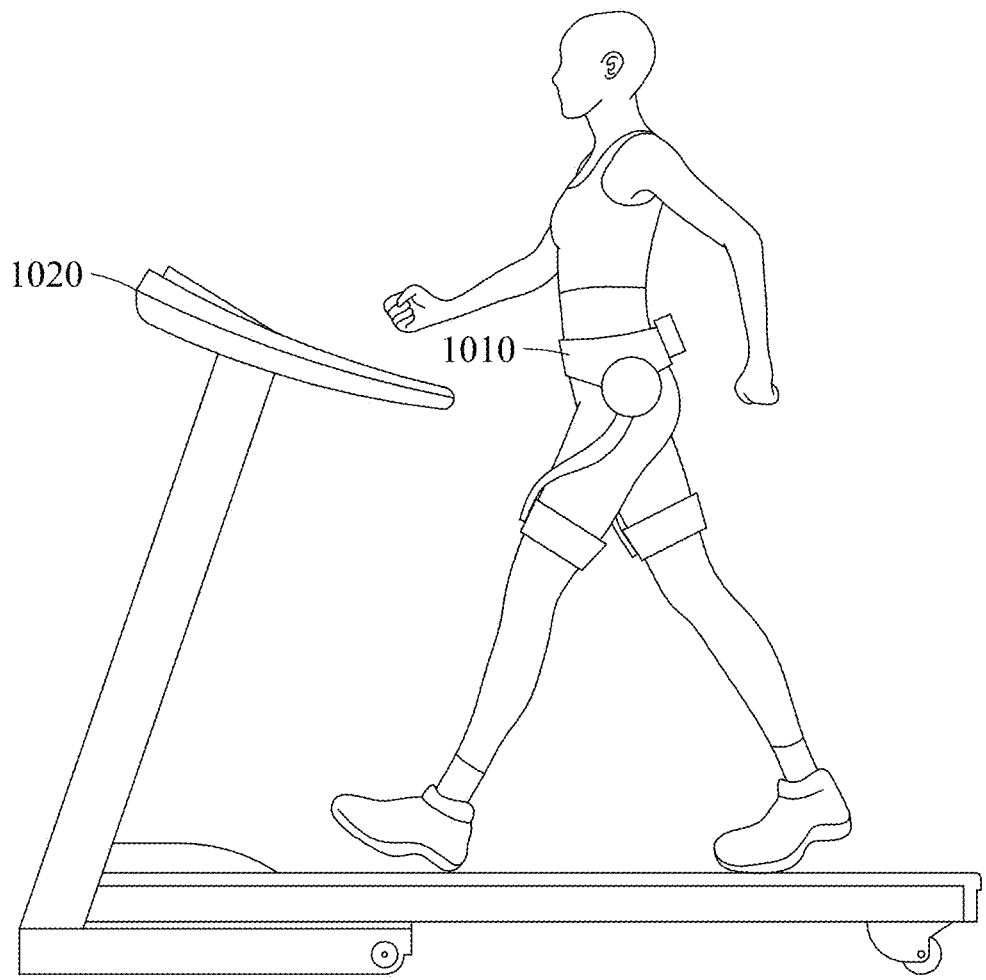
FIG. 10 is a diagram illustrating an example of a balance training method performed using a treadmill according to at least one example embodiment.

FIG. 10 is a diagram illustrating an example of a balance training method performed using a treadmill according to at least one example embodiment.

According to an example embodiment, a balance training method using a wearable device may be performed using other training platforms such as, for example, a treadmill. In such a case, the balance training method may be performed in various ways according to a tool used or an environment in which the balance training method is performed. For example, at a time point at which a user wearing the wearable device climbs steps or a slope while walking on a flat ground, an irregular pattern torque to which a perturbation is applied may be supplied to an actuator of the wearable device, and there may be a sudden change in torque. Referring to FIG. 10, the balance training method using a wearable device 1010 is performed using a treadmill 1020. The treadmill 1020 may provide a function of changing a walking speed or a tilt of a bottom portion thereof. The wearable device 1010 may supply an irregular pattern torque to an actuator at a time point at which the walking speed changes rapidly or the tilt of the bottom portion changes based on the function provided by the treadmill 1020. The wearable device 1010 and/or a remote operation device may control the speed or the tilt of the treadmill 1020. For example, the wearable device 1010 may detect a reaction of the user wearing the wearable device 1010 to the irregular pattern torque, and may increase one or more of the speed and the tilt, in response to detecting that the user remained stable during the irregular pattern torque or may decrease one or more of the speed and the tilt, in response to detecting that the user was unstable during the irregular pattern torque.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A balance training method using a wearable device, comprising:
    generating a walking assistance torque pattern associated with providing a walking assist function to a user wearing the wearable device;
    generating, during a balance training mode of the wearable device, an irregular torque pattern by applying a perturbation to the walking assistance torque pattern that simulates the user falling; and
    instructing an actuator of the wearable device to output a torque based on the walking assistance torque pattern during a first time period and a torque based on the irregular torque pattern during a second time period such that, during the second time period, the torque output by the actuator includes a sudden change in force that simulates the user falling.

2. The balance training method of claim 1, wherein the generating comprises:
    generating the walking assistance torque pattern based on a gait cycle of the user wearing the wearable device;
    determining the perturbation; and
    applying the perturbation to the walking assistance torque pattern.

3. The balance training method of claim 2, wherein the determining the perturbation comprises:
    determining a strength change and an offset change of the perturbation based on an elapsed time, and wherein
        the generating of the irregular torque pattern includes generating the irregular torque pattern by applying, to the walking assistance torque pattern, the strength change and the offset change of the perturbation.

4. The balance training method of claim 1, further comprising:
    detecting a reaction of the user wearing the wearable device to the irregular torque pattern being supplied to the actuator; and adjusting the irregular torque pattern based on the reaction of the user.

5. The balance training method of claim 4, wherein the adjusting comprises:
adjusting at least one of a frequency rate, a strength, or a pattern of the perturbation associated with to the irregular torque pattern.

6. The balance training method of claim 4, wherein the detecting comprises:
determining a recovery index indicating a degree of recovery from the irregular torque pattern based on sensing information measured by the wearable device,
wherein the adjusting adjusts the perturbation associated with the irregular torque pattern, when the recovery index satisfies a set requirement.

7. The balance training method of claim 4, wherein the detecting comprises:
determining a potential fall index indicating a probability of the user falling based on sensing information measured by the wearable device,
wherein the adjusting adjusts a torque to be supplied to the actuator based on a safety torque pattern corresponding to a safety mode of the wearable device, when the potential fall index satisfies a set requirement.

8. The balance training method of claim 4, wherein the detecting comprises:
determining a potential fall index indicating a probability of the user falling based on sensing information measured by the wearable device,
wherein the adjusting includes blocking a torque from being supplied to the actuator, when the potential fall index satisfies a set requirement.

9. The balance training method of claim 1, wherein the instructing comprises:
determining a time point at which the perturbation is to be applied to the irregular torque pattern;
generating the irregular torque pattern by applying the perturbation to the walking assistance torque pattern at the time point; and
instructing the actuator to output the irregular torque pattern.

10. The balance training method of claim 9, wherein the determining of the time point comprises:
determining, to be the time point, a time point at which a step count of the user wearing the wearable device reaches a set step count.

11. The balance training method of claim 9, wherein the determining of the time point comprises:
detecting whether the user wearing the wearable device recovers from the irregular torque pattern and reaches a steady state based on sensing information measured by the wearable device; and
determining, to be the time point, a time point in a time period in which the user wearing the wearable device reaches the steady state.

12. The balance training method of claim 9, wherein the determining of the time point comprises:
determining the time point at which the perturbation is to be applied based on an operation signal received from a remote operation device configured to communicate with the wearable device.

13. The balance training method of claim 1, wherein the perturbation is not applied to the walking assistance torque pattern supplied to the actuator in the first time period.

14. A non-transitory computer-readable medium comprising computer readable instructions to cause a computer to perform the balance training method of claim 1.

15. A wearable device configured to provide a walking assist function, comprising:
a sensor configured to measure a movement of a user wearing the wearable device;
a controller configured to,
generate a walking assistance torque pattern associated with providing a walking assist function to the user wearing the wearable device, and
generate, during a balance training mode of the wearable device, an irregular torque pattern by applying a perturbation to the walking assistance torque pattern that simulates the user falling; and
an actuator configured to output a torque based on the walking assistance torque pattern during a first time period and a torque based on the irregular torque pattern during a second time period such that, during the second time period, the torque output by the actuator includes a sudden change in force that simulates the user falling.

16. The wearable device of claim 15, wherein the controller is configured to:
determine a time point at which the perturbation is to be applied to the irregular torque pattern;
generate the irregular torque pattern by applying the perturbation to a walking assistance torque at the time point; and
supply the irregular torque pattern to the actuator.

17. The wearable device of claim 16, wherein the controller is configured to:
determine, to be the time point, a time point at which a step count of the user wearing the wearable device reaches a set step count or a time point at which the user wearing the wearable device recovers from the irregular torque pattern and reaches a steady state.

18. The wearable device of claim 16, further comprising:
a communicator configured to communicate with a remote operation device,
wherein the controller is configured to determine the time point at which the perturbation is to be applied based on an operation signal received from the remote operation device.

19. The wearable device of claim 15, wherein the controller is configured to:
detect a reaction of the user wearing the wearable device to the irregular torque pattern being supplied to the actuator based on sensing information measured by the sensor; and
adjust the irregular torque pattern based on the reaction of the user.

* * * * *